United States Patent [19]

von der Saal et al.

[11] Patent Number: 4,981,864

[45] Date of Patent: Jan. 1, 1991

[54] METHOD FOR INHIBITION OF ERYTHROCYTE AGGREGATION USING ANELLATED TRICYCLIC COMPOUNDS

[75] Inventors: Wolfgang von der Saal, Weinheim; Alfred Mertens, Schriesheim; Jens-Peter Hoelck, Mannheim; Erwin Boehm, Ladenburg; Ulrich Martin, Mannheim, all of Fed. Rep. of Germany

[73] Assignee: Boehringer Mannehim GmbH, Mannheim, Fed. Rep. of Germany

[21] Appl. No.: 278,190

[22] Filed: Nov. 30, 1988

[30] Foreign Application Priority Data

Dec. 3, 1987 [DE] Fed. Rep. of Germany ....... 3740985

[51] Int. Cl.$^5$ .................. A61K 31/415; A61K 31/54; A61K 31/535; A61K 31/53; A61K 31/50; A61K 31/495; A61K 31/505; A61K 31/44; A61K 31/41; A61K 31/425; A61K 31/42

[52] U.S. Cl. .................... 514/387; 514/183; 514/226.8; 514/228.2; 514/228.5; 514/228.8; 514/232.8; 514/241; 514/242; 514/247; 514/255; 514/256; 514/269; 514/338; 514/361; 514/362; 514/363; 514/375; 514/366; 514/378; 514/381; 514/386; 514/397

[58] Field of Search .................. 514/387; 548/411

[56] References Cited

U.S. PATENT DOCUMENTS

| | | | |
|---|---|---|---|
| 4,666,923 | 5/1987 | Hölck et al. | 514/338 |
| 4,695,567 | 9/1987 | Mertens et al. | 514/253 |
| 4,710,510 | 12/1987 | Mertens et al. | 514/394 |
| 4,730,003 | 3/1988 | von der Saal et al. | 514/387 |
| 4,810,801 | 3/1989 | Mertens et al. | 548/411 |
| 4,831,032 | 5/1989 | von der Saal et al. | 514/254 |
| 4,874,756 | 10/1989 | Mertens et al. | 514/212 |

FOREIGN PATENT DOCUMENTS 0189103 1/1986 European Pat. Off. .
3524067 7/1985 Fed. Rep. of Germany .

OTHER PUBLICATIONS

Chemical Abstracts, vol. 106: 213949k (1987).

Primary Examiner—Douglas W. Robinson
Assistant Examiner—Kevin E. Weddington
Attorney, Agent, or Firm—Felfe & Lynch

[57] ABSTRACT

The present invention is concerned with the use of compounds of the general formula:

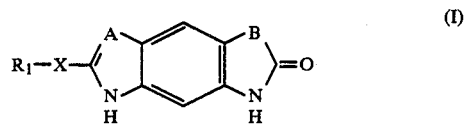

(I)

wherein $R_1$ is a phenyl radical of the general formula:

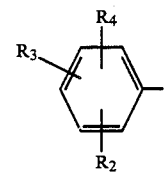

or $R_1$ is a 5 or 6 membered heterocycle or when X is a valency bond $R_1$ is also H, OH, mercapto, amino, alkyl, alkenyl, alkynyl, haloalkyl, alkylthio, formylaminoalkyl, pyridylcarbonylamino, cycloalkyl, or cycloalkenyl, alkoxyalkyl, carboxyalkyl, alkoxycarbonylalkyl or hydroxyalkyl of claim 1 or 2 for the preparation of pharmaceutical compositions with an erythrocyte aggregation inhibition action useful, for example, in states of shock or circulatory disturbance.

11 Claims, No Drawings

METHOD FOR INHIBITION OF ERYTHROCYTE AGGREGATION USING ANELLATED TRICYCLIC COMPOUNDS

The present invention is concerned with the use of compounds of anellated tricyclic compounds as inhibitors of erythrocyte aggregation.

More particularly, the present invention is concerned with the use of compounds of the general formula:

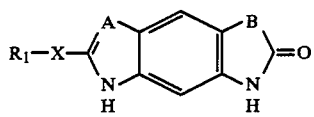

wherein $R_1$ is a phenyl radical of the general formula:

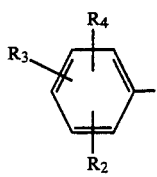

in which $R_2$, $R_3$ and $R_4$, which can be the same or different, are hydrogen atoms, alkanesulphonyloxy, trifluoromethanesulphonyloxy, alkanesulphonylamino, trifluoromethanesulphonylamino, N-alkyl-alkanesulphonylamino, N-alkyl-trifluoromethanesulphonylamino, alkylsulphenylmethyl, alkylsulphinylmethyl or alkylsulphonylmethyl radicals, carbonyl groups substituted by hydroxyl, alkoxy, amino, alkylamino or dialkylamino, sulphonyl groups substituted by amino, alkylamino, dialkylamino or cyclic imino, whereby a methylene group in the 4-position can be replaced by a sulphur or oxygen atom, alkylcarbonylamino, aminocarbonylamino, alkylaminocarbonylamino, alkylthio, alkylsulphinyl or alkylsulphonyl radicals, halogen atoms, nitro, cyano, amino or hydroxyl groups or alkyl, alkoxy, alkenyloxy, alkynyloxy, cyanoalkoxy, carboxyalkoxy, alkoxycarbonylalkoxy, dialkylamino, 1-imidazolyl or trifluoromethyl radicals; or heterocyclic five-membered rings containing up to 4 heteroatoms or heterocyclic six-membered rings containing up to 5 heteroatoms, wherein the heteroatoms can be the same or different and are oxygen, sulphur or nitrogen atoms and, if desired, can carry an oxygen atom on one or more nitrogen atoms, and the five- and six-membered rings can optionally be substituted at least once by alkyl, alkoxy, alkylthio, hydroxyl, nitro, amino, halogen or cyano; or when X represents a valency bond, besides the above-mentioned groups, $R_1$ can also be a hydrogen atom, a hydroxyl, mercapto or amino group or an alkyl, cycloalkyl, alkenyl, cycloalkenyl, alkynyl, haloalkyl, alkoxyalkyl, carboxyalkyl, alkoxycarbonylalkyl, alkylthio, formylaminoalkyl or pyridylcarbonylamino radical, X is a valency bond or an alkylene or vinylene radical, A is a nitrogen atom or a

radical, in which $R_5$ is a hydrogen atom, a cyano group or an alkyl, alkenyl, cycloalkyl, cycloalkenyl, alkylcarbonyl, alkoxycarbonyl, carboxyl, aminocarbonyl, alkylaminocarbonyl, dialkylaminocarbonyl or aryl radical, B is an oxygen or sulphur atom or an $=NR_6$ radical, in which $R_6$ is a hydrogen atom or an alkyl radical, or B can be a $=CR_7R_8$ radical, in which $R_7$ is a hydrogen atom or an alkyl, alkenyl or cycloalkyl radical and $R_8$ is a hydrogen atom, a cyano group, an alkyl or alkenyl radical, a carbonyl group substituted by hydroxyl, alkyl, alkoxy, amino, alkylamino, dialkylamino or hydrazino or $R_7$ and $R_8$ together form an alkylidene or cycloalkylidene radical or $R_7$ and $R_8$, together with the carbon atom to which they are attached, form a spirocycle; and of the tautomers, optically-active forms and racemic mixtures thereof and the physiologically acceptable salts thereof with inorganic and organic acids for the preparation of pharmaceutical compositions with an erythrocyte aggregation-inhibiting action.

The compounds of general formula (I), processes for the preparation thereof and the use thereof as pharmaceuticals are known from European Pat. Specifications Nos. 0,161,632, 0,186,010, 0,189,103, 0,207,483, 0,214,592 and 0,216,165. The compounds are described in these European Patent Specifications as having the following pharmacological actions: increase of the power of the heart, blood pressure lowering, influencing of the thrombocyte aggregation and improvement of the microcirculation.

The compound which are described in the above mentioned applications are primarily useful however for the treatment of such diseases, in which an increase of the power of the heart and a blood pressure lowering is well to the fore, whereby as additional pharmacological effect the improvement of the flow in the microcirculation is achieved by inhibiting of the thrombocyte aggregation on the one hand and by increasing the contractility of the heart on the other hand.

Surprisingly, we have now found that compounds of general formula I possess a marked action with respect to the inhibition of the erythrocyte aggregation. By this, these compounds are also useful for the treatment of diseases, in which the erythrocyte aggregation plays an important part in the pathogenesis, such as, for example, in cases of peripheral, coronary and cerebral circulation disturbances, various types of ulcer, necrotic processes in tumours, degenerative disorders of the retina, nerves and muscles and a wide range of skin disorders. Especially, these compounds can be used for the treatment of arterial occlusion diseases, ischemic disorders, venous insufficiency, or diabetes mellitus. According to the present invention there can be also treated diseases, which are not correlated with a weakening of the heart or an increased blood pressure, but for which a pathologically increased erythrocyte aggregation plays an important part. By this, we have realized a new promising therapeutical principle, because these compounds are the first compounds, which reduce the erythrocyte aggregation at pharmacologically relevant doses, and which are rheologically active.

When, in general formula (II), $R_1$ is a phenyl ring, then the alkyl moieties of the substituents mentioned in the case of $R_2$, $R_3$ and $R_4$ can contain up to 5 and preferably up to 4 carbon atoms. Preferred in this sense are, for example, methanesulphonyloxy, ethanesulphonyloxy, n-propanesulphonyloxy, isopropanesulphonyloxy, trifluoromethanesulphonyloxy, methylsulphenylmethyl, ethylsulphenylmethyl, n-propylsulphenylmethyl, methylsulphinylmethyl, ethylsulphinylmethyl, n-propylsulphinylmethyl, methylsulphonylmethyl, ethylsulphonylmethyl, n-propylsulphonylmethyl, methanesulphonylamino, ethanesulphonylamino, n-propanesulphonylamino, trifluoromethanesulphonylamino, N-methyl-methanesulphonylamino, N-ethyl-methanesulphonylamino, N-methyl-ethanesulphonylamino, N-ethylethanesulphonylamino, N-isopropylethanesulphonylamino, N-methyl-n-propanesulphonylamino, N-n-propyl-propane-sulphonylamino, N-merhyl-trifluoromethanesulphonylamino, N-ethyl-trifluoromethanesulphonylamino, N-isopropyl-trifluoromethanesulphonylamino, methoxycarbonyl, ethoxycarbonyl, propoxycarbonyl, isopropoxycarbonyl, methylaminocarbonyl, ethylaminocarbonyl, dimethylaminocarbonyl, di-n-propylaminocarbonyl, N-methyl -ethylaminocarbonyl, trifluoromethyl, methylaminosulphonyl, ethylaminosulphonyl, n-propylaminosulphonyl, n-butylaminosulphonyl, n-pentylaminosulphonyl, dimethylaminosulphonyl, diethylaminosulphonyl, di-n-propylaminosulphonyl, N-methylisopropylaminosulphonyl, acetylamino, propionylamino, methylcarbonylamino, ethylaminocarbonylamino and propylaminocarbonylamino, methyl, ethyl, propyl, methoxy, ethoxy, propoxy, allyloxy, but-2-enyloxy, but-3-enyloxy, pent-2-enyloxy, propargyloxy, but-2-ynyloxy, but-3-ynyloxy, cyanomethoxy, cyanoethoxy, methoxycarbonylmethoxy, methoxycarbonylethoxy, methylthio, ethylthio, methylsulphinyl, ethylsulphinyl, methylsulphonyl and ethylsulphonyl radicals.

Sulphonyl groups substituted by cyclic amino are preferably morpholino, thiomorpholino, pyrrolidino, piperidino and hexamethyleneiminosulphonyl groups.

In particular, $R_2$ is preferably a hydrogen atom or an alkylsulphonyloxy, trifluoromethylsulphonyloxy, alkylsulphenylmethyl, alkylsulphinylmethyl, alkylsulphonylmethyl, alkylsulphonylamino, N-alkylalkylsulphonylamino, trifluoromethylsulphonylamino or N-alkyl-trifluoromethylsulphonylamino radical, a carbonyl group substituted by hydroxyl, alkoxy, amino, alkylamino or dialkylamino or a sulphonyl group substituted by amino, dialkylamino or morpholino, in which each of the above-mentioned alkyl moieties can contain 1 or 2 carbon atoms, a nitro or cyano group or an alkylaminosulphonyl radical containing up to 4 carbon atoms, an alkylcarbonylamino, aminocarbonylamino or N-alkyl-aminocarbonylamino radical, an alkylthio, alkylsulphinyl or alkylsulphonyl radical, in which each of the above-mentioned alkyl moieties can contain 1 or 2 carbon atoms, a halogen atom, an amino or hydroxyl group or a dialkylamino, alkyl, alkoxy, alkenyloxy or alkynyloxy radical, preferably containing up to 3 carbon atoms, or a cyanomethoxy, methoxycarbonylmethoxy, trifluoromethyl or 1-imidazolyl radical, $R_3$ is preferably a hydrogen or halogen atom, an alkyl radical containing up to 3 carbon atoms or an alkoxy or dialkylamino radical containing 1 or 2 carbon atoms in each alkyl moiety and $R_4$ is a hydrogen atom or a methoxy radical.

The phenyl radical can contain 1 to 3 of these substituents.

Preferred monosubstituted phenyl compounds are the hydroxy-, $C_1-C_3$-alkyl-, $C_1-C_3$-alkoxy-, allyloxy-, propargyloxy-, cyanomethoxy-, methoxycarbonylmethoxy-, halo-, nitro-, cyano-, aminocarbonyl-, methoxycarbonyl-, amino-, $C_1-C_3$-dialkylamino-, $C_1-C_3$-alkylthio -, $C_1-C_3$-alkylsulphinyl-, $C_1-C_3$-alkylsulphonyl-, $C_1-C_3$-alkyl- sulphonyloxy- and 1-imidazolyl-phenyls, in which case the substituent can be in the 2-, 3- or 4-position.

Preferred disubstituted phenyls contain as substituents alkanesulphonyloxy, trifluoromethylsulphonyloxy, alkylsulphenylmethyl, alkylsulphinylmethyl, alkylsulphonylmethyl, alkylsulphonylamino, N-alkyl-alkylsulphonylamino, trifluoromethylsulphonylamino or N-alkyl-trifluoromethylsulphonylamino radicals, carbonyl groups substituted by hydroxy, alkoxy, amino, alkylamino or dialkylamino or sulphonyl groups substituted by amino, dialkylamino or morpholino, alkylaminosulphonyl, alkylcarbonylamino, aminocarbonylamino or N-alkyl-aminocarbonylamino radicals, halogen atoms, hydroxyl, cyano, nitro or amino groups, alkyl, alkoxy, allyloxy, propargyloxy, cyanomethoxy, methoxycarbonylmethoxy, dialkylamino, alkylthio, alkylsulphinyl, alkylsulphonyl or 1-imidazolyl radicals, in which the two substituents can be the same or different and can be in the 2,3-, 2,4-, 2,5-, 2,6-, 3,4- and 3,5-positions but preferably in the 2,4-, 2,5- and 3 4-positions and said alkyl radicals, alone or in combination with other radicals, can contain up to 3 carbon atoms.

Preferred trisubstituted phenyls contain hydroxyl groups and methoxy radicals as substituents.

When $R_1$ signifies a heterocyclic five-membered ring containing up to 4 hetero atoms or a heterocyclic six-membered ring containing up to 5 heteroatoms, in which the heteroatoms in the said five- and six-membered rings can be the same or different and are nitrogen, oxygen or sulphur atoms and one or more of the nitrogen atoms can optionally carry an oxygen atom, then preferred in this sense are the pyrrole, furan, thiopb.ene, pyrazole, imidazole, thiazole, isothiazole, oxazole, isoxazole, triazole, tetrazole, thiadiazole, oxadiazole, pyrazine, N,N'-dioxypyrazine, pyrimidine, N,N'-dioxypyrimidine, pyridazine, oxazine, thiazine, triazine, tetrazine, pyridine and N-oxypyridine radicals.

Alkyl, alkoxy and alkylthio substituents in the heterocyclic five- and six-membered rings can contain up to 6 and preferably up to 4 carbon atoms, the methyl, ethyl, methoxy, ethoxy, methylthio and ethylthio radicals being preferred. Halogen is to be understood to be a fluorine, chlorine or bromine atom, chlorine being preferred.

If X is a valency bond and $R_1$ is an alkyl, alkenyl or alkynyl radical, then straight-chained and branched chains containing up to 8 carbon atoms are thereby to be understood. Preferred in this sense are methyl, ethyl, propyl, butyl, pentyl, hexyl, vinyl, propenyl and propynyl radicals.

If X is a valency bond and $R_1$ is a cycloalkyl or cycloalkenyl radical, then there are thereby to be understood rings containing 3 to 6 members. Preferred in this sense are the cyclopropyl, cyclobutyl, cyclopentyl, cyclohexyl, cyclopentenyl and cyclohexenyl radicals.

If X is a valency bond and $R_1$ an alkoxyalkyl, carboxyalkyl, alkoxycarbonylalkyl or hydroxyalkyl radical, then the alkyl and alkoxy moieties can contain up to 6 carbon atoms. Preferred in this sense are the ethoxymethyl, methoxyethyl, ethoxyethyl, carboxymethyl, carboxypropyl, carboxybutyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylethyl, hydroxymethyl, hydroxyethyl, hydroxypropyl and hydroxybutyl radicals.

X is preferably a valency bond or a methylene, ethylene or vinylene radical.

If A is

radical and $R_5$ is an alkyl-carbonyl, alkoxycarbonyl, aminocarbonyl, alkylaminocarbonyl or dialkylaminocarbonyl radical, then the alkyl and alkoxy moieties can contain up to 7 and preferably up to 5 carbon atoms, the acetyl, propionyl, methoxycarbonyl, ethoxycarbonyl, aminocarbonyl, methylaminocarbonyl and dimethylaminocarbonyl radicals thereby being preferred.

If B signifies an $=NR_6$ radical and $R_6$ an alkyl radical, then methyl, ethyl, propyl, isopropyl, butyl, 2-butyl and 1,1-dimethylethyl radicals are preferred.

If B is a $=CR_7R_8$ radical and $R_7$ and/or $R_8$ is an alkyl, cycloalkyl, alkenyl radical or a carbonyl group substituted by alkyl, alkoxy, alkylamino or dialkylamino, then each of the alkyl and alkenyl moieties can be straight-chained or branched and contains 1 to 6 or 2 to 6 carbon atoms, respectively, and the cycloalkyl moiety contains 3 to 7 carbon atoms.

Preferred in this sense for $R_7$ is a hydrogen atom or a methyl, ethyl, isopropyl, 3-pentyl, cyclopentyl or cyclohexyl radical. $R_8$ is preferably a hydrogen atom, a cyano or carboxyl group or a methyl, ethyl, isopropyl, 3-pentyl, acetyl, propynyl, methoxycarbonyl, ethoxycarbonyl, aminocarbonyl, methylaminocarbonyl, dimethylaminocarbonyl or hydrazinocarbonyl radical.

If $R_7$ and $R_8$, together with the carbon atom to which they are attached, form a cycloalkyl ring, then this is preferably a spirocyclopropyl, spirocyclobutyl, spirocyclopentyl or spirocyclohexyl ring. If $R_7$ and $R_8$ together form an alkylidene or cycloalkylidene radical, then the isopropylidene and cyclohexylidene rings are preferred.

Especially preferred are compounds of general formula (I), wherein $R_1$ is a phenyl radical of general formula (II) in which $R_2$ is a hydrogen or chlorine atom, a cyano, nitro or amino group or a methanesulphonyloxy, trifluoromethanesulphonyloxy, methanesulphonylamino, trifluoromethanesulphonylamino, methanesulphonylmethylamino, trifluoromethanesulphonylmethylamino, methylsulphinylmethyl, methylsulphonylmethyl, aminocarbonyl, aminosulphonyl, methylaminosulphonyl, dimethylaminosulphonyl, acetylamino, methylthio, methylsulphinyl, methylsulphonyl, hydroxyl, allyloxy, methyl, methoxy, propargyloxy, cyanomethoxy, methoxycarbonylmethoxy, dimethyylamino, trifluoromethyl or 1-imidazolyl radical, $R_3$ is a hydrogen or chlorine atom, a hydroxyl group or a methyl, methoxy or dimethylamino radical and $R_4$ is a hydrogen atom or a methoxy radical or $R_1$ is a pyrrole, furan, thiophene, pyrazole, imidazole, isothiazole, thiazole, oxazole, triazole, tetrazole, thiadiazole, isoxazole, oxadiazole, pyridine, N-oxypyridine, pyrazine, pyrimidine, N,N'-dioxypyrimidine, pyridazine, oxazine, thiazine, triazine or tetrazine radical or a methyl-, ethyl-, methoxy-, ethoxy-, methylthio-, ethylthio- or chloro-substituted derivative thereof or, when X is a valency bond, besides the above-mentioned groups, $R_1$ can also be a hydrogen atom, a hydroxyl, mercapto or amino group or a methyl, ethyl, propyl, butyl, pentyl, hexyl, propenyl, cyclopentyl, cyclohexyl, trifluoromethyl or methylthio radical, X is a valency bond or an ethylene or vinylene radical, A is a nitrogen atom or a

radical, B is an oxygen or sulphur atom or an $=NR_6$ radical, in which $R_6$ is a methyl, ethyl or propyl radical or B is a $=CR_7R_8$ radical, in which $R_7$ is a hydrogen atom or a methyl radical and $R_8$ is a methyl, ethyl or isopropyl radical or $R_7$ and $R_8$, together with the carbon atom to which they are attached, form a spirocyclopentyl ring.

For the preparation of pharmaceutical compositions, the compounds of general formula (I) are mixed in known manner with appropriate pharmaceutical carrier materials, aroma, flavouring and colouring materials and formed, for example, into tablets or dragees or, with the addition of appropriate adjuvants, are suspended or dissolved in water or in an oil, for example olive oil.

The compounds of general formula (I) and the salts thereof canbe administered enterally or parenterally in liquid or solid form, As injection medium, it is preferred to use water which contains the additives usual in the case of injection solutions, such as stabilising agents, solubilising agents and buffers.

Such additives include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycol). Compositions suitable for oral administration can, if desired, contain flavouring and sweetening agents.

The compounds are usually administered in amounts of from 10 to 2000 mg. per day, referred to a body weight of 75 kg. It is preferred to administer 1 or 2 tablets which have an active material content of from 5 to 500 mg. 2 or 4 times a day. The tablets can also be retarded, in which case only 1 or 2 tablets with an active material content of from 20 to 1000 mg. have to be administered once per day. The active material can also be administered by injection 1 to 8 times a day or by continuous infusion, in which case 10 to 1000 mg. per day normally suffice.

The determination of the erythrocyte aggregation takes place with a mini-erythrocyte aggregometer of the firm Myrenne, Rotgen (see Kiesewetter et al., Biomed. Tecknik, 27, 209–213/1982). As a measure, this apparatus gives a dimensionless index which increases with increasing aggregation tendency.

The investigations were carried out with human blood from healthy donors. The blood was adjusted to a haematocrit of 45% and incubated with a control solution or with a solution of a test substance. The erythrocyte aggregation was then measured. Each compound was investigated in a concentration of $10^{-5}$ molar. Per compound there were carried out two investigations with the blood from two donors. There was calculated the difference of the aggregation indices between the initial value of the control solution and the values with the solutions of the test compounds ($\Delta E$).

In the following Table, there are set out the findings obtained for the erythrocyte aggregation ($\Delta E$). The lower is the given value, the more effective is the test compound. On the other hand, venoruton, a mixture of various O-($\beta$-hydroxyethyl)-rutosides, at a comparable concentration of $1.7 \times 10^{-5}$M, only brings about a change of the erythrocyte aggregation index of $-0.4$. Even at a concentration of $1.7 \times 10^{-3}$M, the change only amounts to $-3.9 \pm 0.9$. Venoruton is said to inhibit the tendency towards erythrocyte aggregation (see Schmid-Schonbeim et al., VASA, 4, 263–270/1975).

In comparison with the prior art, the compounds used according to the present invention clearly inhibit the erythrocyte aggregation more strongly.

It will be understood that the specification and examples are illustrative but not limitative of the present invention and that other embodiments within the spirit and scope of the invention will suggest themselves to those skilled in the art.

| No. | compound | m.p. (°C.) | $\Delta E$ [$10^{-5}$ M] |
|---|---|---|---|
| 1 | 7,7-dimethyl-2-(4-pyridyl)-6,7-dihydro-3H,5H-pyrrolo[2,3-f]benzimidazol-6-one × 4 H$_2$O | 215 | $-8$ |
| 2 | 7,7-dimethyl-2-(2-pyridyl)-6,7-dihydro-3H,5H-pyrrolo[2,3-f]benzimidazol-6-one × 0.3 H$_2$O | 182–187 | $-4$ |
| 3 | 7,7-dimethyl-2-(3-pyridyl)-6,7-dihydro-3H,5H-pyrrolo[2,3-f]benzimidazol-6-one × 4 H$_2$O | 331–335 | $-4$ |
| 4 | 7,7-dimethyl-2-(4-(2-methylpyridyl)-6,7-dihydro-3H,5H-pyrrolo[2,3-f]benzimidazol-6-one × 0.6 H$_2$O | 311–313 | $-9$ |
| 5 | 7,7-dimethyl-2-(4-(2-hydroxypyridyl))-6,7-dihydro-3H,5H-pyrrolo[2,3-f]benzimidazol-6-one × 2 H$_2$O | >360 | $-1$ |
| 6 | 7,7-dimethyl-2-(4-(2-chloropyridyl))-6,7-dihydro-3H,5H-pyrrolo[2,3-f]benzimidazol-6-one | 341–344 | $-11$ |
| 7 | 7,7-dimethyl-2-(2-(3-pyridyl)-ethenyl)-6,7-dihydro-3H,5H-pyrrolo[2,3-f]benzimidazol-6-one × 0.6 H$_2$O | 203–207 | $-8$ |
| 8 | 7,7-dimethyl-2-(2-(4-pyridyl)-ethyl)-6,7-dihydro-3H,5H-pyrrolo[2,3-f]benzimidazol-6-one | 150–154 | $-1$ |
| 9 | 2'-(4-pyridyl)-spiro[cyclopentan-1,7',6,7'-dihydro-3'H,5'H-pyrrolo[2',3'-f]-benzimidazol 6'-one × 0.3 | >365 | $-9$ |
| 10 | 7,7-dimethyl-2-(3-(6-methylpyridyl))-6,7-dihydro-3H,5H-pyrrolo[2,3-f]benzimidazol-6-one | >360 | $-4$ |
| 11 | 7,7-dimethyl-2-(3-(2-methoxy-6-methyl)-pyridyl)-6,7-dihydro-3H,5H-pyrrolo[2,3-f]benzimidazol-6-one | 296–298 | $-9$ |
| 12 | 7,7-dimethyl-2-(4-N-oxypyridyl)-6,7-dihydro-3H,5H-pyrrolo[2,3-f]benzimidazol-6-one × 3 H$_2$O | 260–262 | $-2$ |
| 13 | 7-ethyl-2-(4-pyridyl)-6,7-dihydro-3H,5H-pyrrolo[2,3-f]benzimidazol-6-one | 270–272 | $-2$ |
| 14 | 7-ethyl-2-(3-pyridyl)-6,7-dihydro-3H,5H-pyrrolo[2,3-f]benzimidazol-6-one | >300 | $-2$ |
| 15 | 7-(2-propyl)-2-(4-pyridyl)-6,7-dihydro-3H,5H-pyrrolo[2,3-f]benzimidazol-6-one | 215–220 | $-2$ |
| 16 | 7-cyclopentyl-2-(4-pyridyl)-6,7-dihydro-3H,5H-pyrrolo[2,3-f]benzimidazol-6-one | 200–204 | $-2$ |
| 17 | 7,7-diethyl-2-(4-pyridyl)-6,7-dihydro-3H,5H-pyrrolo[2,3-f]benzimidazol-6-one | 216–219 | $-5$ |
| 18 | 7-ethoxycarbonyl-7-methyl-2-(4-pyridyl)-6,7-dihydro-3H,5H-pyrrolo[2,3-f]benzimidazol-6-one × HCl | 288–290 | $-2$ |
| 19 | 7-(2-methylpropyl)-2-(4-pyridyl)-6,7-dihydro-3H,5H-pyrrolo[2,3-f]benzimidazol-6-one × 1.5 H$_2$O | 200–202 | $-1$ |
| 20 | 7,7-dimethyl-2-(4-(3-hydroxypyridyl)-6,7-dihydro-3H,5H-pyrrolo[2,3-f]benzimidazol-6-one | >300 | $-8$ |
| 21 | 7,7-dimethyl-2-(2-(5-n-butylpyridyl))-6,7-dihydro-3H,5H-pyrrolo[2,3-f]benzimidazol-6-one | 176–178 | $-7$ |
| 22 | 7,7-dimethyl-2-(2-furanyl)-6,7-dihydro-3H,5H-pyrrolo[2,3-f]benzimidazol-6-one | 311–316 | $-5$ |
| 23 | 7,7-dimethyl-2-(2-thienyl)-6,7-dihydro-3H,5H-pyrrolo[2,3-f]benzimidazol-6-one | 322–336 | $-8$ |
| 24 | 7,7-dimethyl-2-(2-pyrazinyl)-6,7-dihydro-3H,5H-pyrrolo[2,3-f]benzimidazol-6-one | >300 | $-2$ |
| 25 | 7,7-dimethyl-2-(4-thiazolyl)-6,7-dihydro-3H,5H-pyrrolo[2,3-f]benzimidazol-6-one | 280 | $-3$ |
| 26 | 7,7-dimethyl-2-(2-methylpyrimidin-5-yl)-6,7-dihydro-3H,5H-pyrrolo[2,3-f]benzimidazol-6-one | >350 | $-4$ |
| 27 | 7,7-dimethyl-2-(1,2,4-1H-triazol-3-yl)-6,7-dihydro-3H,5H-pyrrolo[2,3-f]benzimidazol-6-one | >350 | $-3$ |
| 28 | 7,7-dimethyl-2-(2-methyloxazol-4-yl)-6,7-dihydro-3H,5H-pyrrolo[2,3-f]benzimidazol-6-one | 315–318 | $-2$ |
| 29 | 7-methyl-7-ethoxycarbonyl-2-(2-pyrazinyl)-6,7-dihydro-3H,5H-pyrrolo[2,3-f]benzimidazol-6-one | 213–214 | $-3$ |
| 30 | 7,7-dimethyl-2-(2-thienylmethyl)-6,7-dihydro-3H,5H-pyrrolo[2,3-f]benzimidazol-6-one | 233–235 | $-3$ |
| 31 | 7,7-dimethyl-2-(1,2,3-thiadiazol-4-yl)-6,7-dihydro-3H,5H-pyrrolo[2,3-f]benzimidazol-6-one | >300 | $-3$ |
| 32 | 7,7-dimethyl-2-(1,2,3-thiadiazol-5-yl)-6,7-dihydro-3H,5H-pyrrolo[2,3-f]benzimidazol-6-one | 286–290 | $-9$ |
| 33 | 7,7-dimethyl-2-(2-methylthio-1,3,4-oxadiazol-5-yl)-6,7-dihydro-3H,5H-pyrrolo[2,3-f]benzimidazol-6-one | 311 | $-3$ |
| 34 | 7,7-dimethyl-2-(4-methoxycarbonyl-1,2,3-1H-triazol-5-yl)-6,7-dihydro-3H,5H-pyrrolo[2,3-f]benzimidazol-6-one | >300 | $-1$ |
| 35 | 2'-(4-pyridazinyl)-spiro[cyclopentane-1,7'-6,7'- | 365–367 | $-8$ |

-continued

| No. | compound | m.p. (°C.) | ΔE [$10^{-5}$ M] |
|---|---|---|---|
|  | dihydro-3'H,5'H-pyrrolo-[2',3'-f]benzimidazol]-6'-one |  |  |
| 36 | 7-ethyl-2-(4-pyridazinyl)-6,7-dihydro-3H,5H-pyrrolo-[2,3-f]benzimidazol-6-one | >300 | −5 |
| 37 | 2'-(2-furanyl)-spiro[cyclopentane-1,7'-6',7'-dihydro-3'H,5'H-pyrrolo[2',3'-f]-benzimidazol]-6'-one | >300 | −9 |
| 38 | 7,7-dimethyl-2-(4-nitrophenyl)-6,7-dihydro-3H,5H-pyrrolo[2,3-f]benzimidazol-6-one | >300 | −5 |
| 39 | 7,7-dimethyl-2-(4-aminophenyl)-6,7-dihydro-3H,5H-pyrrolo[2,3-f]benzimidazol-6-one | 225–230 | −6 |
| 40 | 7,7-dimethyl-2-(2-hydroxyphenyl)-6,7-dihydro-3H,5H-pyrrolo[2,3-f]benzimidazol-6-one | 371–373 | −9 |
| 41 | 7,7-dimethyl-2-(3,4-dichlorophenyl)-6,7-dihydro-3H,5H-pyrrolo[2,3-f]benzimidazol-6-one | >300 | −10 |
| 42 | 7,7-dimethyl-2-(2-phenylvinyl)-6,7-dihydro-3H,5H-pyrrolo[2,3-f]benzimidazol-6-one | 320–325 | −10 |
| 43 | 7,7-dimethyl-2-(2-methoxy-4-methylsulphinylphenyl)-6,7-dihydro-3H,5H-pyrrolo-[2,3-f]benzimidazol-6-one | 217–220 | −10 |
| 44 | 7,7-dimethyl-2-(4-trifluoromethylphenyl)-6,7-dihydro-3H,5H-pyrrolo[2,3-f]benzimidazol-6-one | >300 | −7 |
| 45 | 2'-phenyl-spiro[cyclopentane-1,7'-6',7'-dihydro-3'H,5'H-pyrrolo[2',3'-f]-benzimidazol]-6'-one | 353–355 | −10 |
| 46 | 2'-(2-methoxy-4-hydroxyphenyl)-spiro[cyclopentane-1.7'-6',7'-dihydro-3'H,5'H-pyrrolo[2',3'-f]benzimidazol]-6'-one | 335–340 | −5 |
| 47 | 2'-(2-methoxy-4-methylsulphonylphenyl)-spiro-[cyclopentane-1,7'-6',7'-dihydro-3'H,5'H-pyrrolo-[2',3'-f]benzimidazol]-6'-one | 270–272 | −5 |
| 48 | 7-isopropyl-2-(4-methoxyphenyl)-6,7-dihydro-3H,5H-pyrrolo[2,3-f]benzimidazol-6-one | 326–328 | −8 |
| 49 | 7,7-dimethyl-2-phenylmethyl-6,7-dihydro-3H,5H-pyrrolo-[2,3-f]benzimidazol-6-one | 328–330 | −1 |
| 50 | 7,7-dimethyl-2-(2-methoxyphenyl)-6,7-dihydro-3H,5H-pyrrolo[2,3-f]benzimidazol-6-one | 300–303 | −10 |
| 51 | 7,7-dimethyl-2-(4-methoxyphenyl)-6,7-dihydro-3H,5H-pyrrolo[2,3-f]benzimidazol-6-one | 341–343 | −7 |
| 52 | 7,7-dimethyl-2-(4-chlorophenyl)-6,7-dihydro-3H,5H-pyrrolo[2,3-f]benzimidazol-6-one | 360–363 | −3 |
| 53 | 7,7-dimethyl-2-(2-methoxy-5-methylsulphonylphenyl)-6,7-dihydro-3H,5H-pyrrolo-[2,3-f]benzimidazol-6-one | 236–238 | −2 |
| 54 | 7,7-dimethyl-2-(4-methylphenyl)-6,7-dihydro-3H,5H-pyrrolo[2,3-f]benzimidazol-6-one | >300 | −10 |
| 55 | 7,7-diethyl-2-(4-methoxyphenyl)-6,7-dihydro-3H,5H-pyrrolo[2,3-f]benzimidazol-6-one | 217–219 | −4 |
| 56 | 2'-(4-methoxyphenyl)-spiro-[cyclopentane-1,7'-6',7'-dihydro-3'H,5'H-pyrrolo-[2',3'-f]benzimidazol]-6'-one | 354–355 | −10 |
| 57 | 7-methyl-2-(2,4-dimethoxyphenyl)-6,7-dihydro-3H,5H-pyrrolo[2,3-f]benzimidazol-6-one | 294–297 | −2 |
| 58 | 7,7-dimethyl-2-(4-hydroxyphenyl)-6,7-dihydro-3H,5H-pyrrolo[2,3-f]benzimidazol-6-one | 240 | −12 |
| 59 | 7,7-dimethyl-2-phenyl-6,7-dihydro-3H,5H-pyrrolo-[2,3-f]benzimidazol-6-one | 195–220 | −8 |
| 60 | 7,7-dimethyl-2-(2,4-dimethoxyphenyl)-6,7-dihydro-3H,5H-pyrrolo-[2,3-f]benzimidazol-6-one | 294–297 | −10 |
| 61 | 7,7-dimethyl-2-(3,4-dimethoxyphenyl)-6,7-dihydro-3H,5H-pyrrolo-[2,3-f]benzimidazol-6-one | 314–317 | −14 |
| 62 | 7,7-dimethyl-2-(2-methoxy-4-chlorophenyl)-6,7-dihydro-3H,5H-pyrrolo[2,3-f]benzimidazol-6-one | 299–301 | −13 |
| 63 | 7,7-dimethyl-2-[4-(1H-imidazol-1-yl)-phenyl]-6,7-dihydro-3H,5H-pyrrolo[2,3-f]-benzimidazol-6-one | 300 | −11 |
| 64 | 7,7-dimethyl-2-(4-dimethylaminophenyl)-6,7-dihydro-3H,5H-pyrrolo[2,3-f]benzimidazol-6-one | 262–270 | −8 |
| 65 | 7,7-dimethyl-2-(2-methoxy-4-methylsulphonylphenyl)-6,7-dihydro-3H,5H-pyrrolo[2,3-f]-benzimidazol-6-one | 233–235 | −8 |
| 66 | 7-ethoxycarbonyl-7-methyl-2-phenyl-6,7-dihydro-3H,5H-pyrrolo[2,3-f]benzimidazol-6-one | 178–182 | −3 |
| 67 | 7,7-dimethyl-2-(2-methoxy-4-methylsulphonylphenyl)-6,7-dihydro-3H,5H-pyrrolo-[2,3-f]benzimidazol-6-one | 235–237 | −10 |
| 68 | 6-phenyl-1-methyl-1,2,3,5-tetrahydrobenzo[1,2-d: 4,5-d']diimidazol-2-one | >300 | −1 |
| 69 | 6-(4-dimethylaminophenyl)-1-methyl-1,2,3,5-tetrahydrobenzo[1,2-d:4,5-d']diimidazol-2-one | 238–241 | −5 |
| 70 | 6-(4-(1-imidazolyl)-phenyl)-1-methyl-1,2,3,5-tetrahydrobenzo[1,2-d:4,5-d']-diimidazol-2-one | 260 (decomp.) | −5 |
| 71 | 6-(4-diethylamino-2-methoxyphenyl)-1-methyl-1,2,3,5-tetrahydrobenzo[1,2-d: 4,5-d']diimidazol-2-one | >300 | −9 |
| 72 | 6-(4-pyridyl)-1-ethyl-1,2,3,5-tetrahydrobenzo-[1,2-d:4,5-d']diimidazol-2-one | 237–239 | −3 |
| 73 | 6-(4-pyridyl)-1-(1-propyl)-1,2,3,5-tetrahydrobenzo-[1,2-d:4,5-d']diimidazol-2-one | 235–237 | −5 |
| 74 | 6-(4-pyridazinyl)-1-methyl-[1,2,3,5-tetrahydrobenzo-[1,2-d:4,5-d']diimidazol-2-one | >300 | −2 |
| 75 | 6-(4-pyridazinyl-1-ethyl- | >300 | −4 |

| No. | compound | m.p. (°C.) | ΔE [$10^{-5}$ M] |
|---|---|---|---|
| | 1,2,3,5-tetrahydrobenzo-[1,2-d:4,5-d']diimidazol-2-one | | |
| 76 | 6-(3-thienyl)-2,3-dihydro-5H-imidazol[4,5-f]benzoxazol 2-one | 295–300 | −2 |
| 77 | 6-(4-pyridyl)-2,3-dihydro-5H-imidazo[4,5-f]benz-thiazol-2-one | >300 | |
| 78 | 6-pyrazinyl-2,3-dihydro-5H-imidazo[4,5-f]benzoxazol-2-one | 335 | −2 |
| 79 | 6-(2-methylthiophenyl)-2,3-dihydro-5H-imidazo[4,5-f]-benzoxazol-2-one | 208–211 | −2 |
| 80 | 6-(2-methoxyphenyl)-2,3-dihydro-5H-imidazo[4,5-f]-benzoxazol-2-one | 319–321 | −5 |
| 81 | 6-phenyl-2,3-dihydro-5H-imidazo[4,5-f]benzoxazol-2-one | 298–300 | −4 |
| 82 | 6-(2-methyl-4-pyridyl)-2,3-dihydro-5H-imidazo[4,5-f]-benzoxazol-2-one | >300 | −3 |
| 83 | 6-(1-propyl)-2,3-dihydro-5H-imidazo[4,5-f]benzoxazol-2-one | 177–180 | −2 |
| 84 | 3,3-dimethyl-6-(4-pyridyl)-benzo[1,2-b:5,4-b']dipyrrol-2-(1H,3H,7H)-one | >300 | −3 |
| 85 | 3,3-dimethyl-6-(3-pyridyl)-benzo[1,2-b:5,4-b']dipyrrol-2-1H,3H,7H)-one × CH3OH | 305 | −6 |
| 86 | 3,3-dimethyl-6-[4-(1H-imidazol-1-yl-phenyl]-benzo-[1,2-b:5,4-b']dipyrrol-2-(1H,3H,7H)-one | >340 | −6 |
| 87 | 3-methyl-6-(3-pyridyl)-benzo-[1,2-b:5,4-b']dipyrrol-2-(1H,3H,7H)-one | 330–331 | −2 |
| 88 | 3-methyl-6-(3-pyridyl)-benzo-[1,2-b:5,4-b']dipyrrol-2-(1H,3H,7H)-one | 270–273 | −10 |
| | 3,3-dimethyl-6-(4-methyl-phenyl)-benzo[1,2-b:5,4-b']-dipyrrol-2-(1H,3H,7H)-one | 278–281 | −4 |
| 90 | 7,7-dimethyl-2-cyclohexyl-6,7-dihydro-3H,5H-pyrrolo-[2,3-f]benzimidazol-6-one | 315–318 | −4 |
| 91 | 2'-propyl-spiro[cyclopentan-1,7'-6',7'-dihydro-3'H,5'H-pyrrolo[2',3'-f]benz-imidazol]-6'-one | 332–335 | −6 |
| 92 | 2-(1-propenyl)-7,7-dimethyl-6,7-dihydro-3H,5H-pyrrolo-[2,3-f]benzimidazol-6-one | 252–254 | −7 |
| 93 | 2-n-hexyl-7,7-dimethyl-6,7-dihydro-3H,5H-pyrrolo-[2,3-f]benzimidazol-6-one | 233–234 | −8 |
| 94 | 7,7-dimethyl-2-(1-cyclo-penten-1-yl)-6,7-dihydro-3H,5H-pyrrolo[2,3-f]benz-imidazol-6-one | 233–235 | −6 |
| 95 | 2-(4-pyridylcarbonylamino)-7,7-dimethyl-6,7-dihydro-3H,5H-pyrrolo[2,3-f]benz-imidazol-6-one | >300 | −7 |
| 96 | 2'-(4-Ethoxyphenyl)spiro [cyclo-pentan-1,7'-6',7'-dihydro-3'H,5'H-pyrrolo [2',3'-f]-benzimidazol-6'-on, prepared according to EP 186 010 | >300 | −9 |

What is claimed:

1. A method for the inhibition of erythrocyte aggregation which comprises treating patients with conditions having need of such inhibition with an effective amount of a compound of the formula:

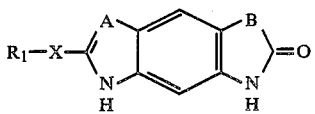
(I)

wherein $R_1$ is a phenyl of the formula:

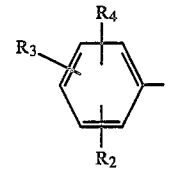
(II)

wherein $R_2$, $R_3$, $R_4$, which can be the same or different, are hydrogen, $C_1$–$C_5$ alkanesulphonyloxy, trifluormethanesulphonyloxy, $C_1$–$C_5$ alkanesulphonylamino, trifluorometanesulphonylamino, $C_1$–$C_5$ N-alkyl-$C_1$–$C_5$-alkanesulphonylamino, $C_1$–$C_5$ N-alkyl-trifluoromethanesulphonylamino, $C_1$–$C_5$ alkylsulphenylmethyl, $C_1$–$C_5$ alkylsulphinylmethyl, $C_1$–$C_5$ alkylsulphonylmethyl or, carbonyl groups substituted by hydroxyl $C_1$–$C_5$-alkoxy amino $C_1$–$C_5$-alkylamino, di-$C_1$–$C_5$-alkylamino, or sulphonyl groups substituted by amino, $C_1$–$C_5$-alkylamino, di-$C_1$–$C_5$-alkylamino or cyclic imino, wherein a methylene group in the 4-position of the cyclic imino can be replaced by a sulphur or oxygen atom, or $C_1$–$C_5$ alkyl-carbonylamino, aminocarbonylamino, $C_1$–$C_5$-alkyl-aminocarbonylamino, $C_1$–$C_5$-alkylthio, $C_1$–$C_5$-alkylsulphinyl, $C_1$–$C_5$-alkylsulphonyl, or halogen, nitro, cyano, amino, hydroxyl, $C_1$–$C_5$-alkoxy, $C_1$–$C_5$ -alkyl, $C_2$–$C_5$-alkenyloxy, $C_2$–$C_5$-alkynyloxy, cyano-$C_1$–$C_5$alkoxy, carboxy-$C_1$–$C_5$-alkoxy, $C_1$–$C_5$ -alkoxycarbonyl-$C_1$–$C_5$alkoxy, di-$C_1$–$C_5$-alkylamino, 1-imidazolyl, trifluoromethyl; or $R_1$ is a heterocyclic five-membered ring containing up to 4 heteroatoms, or heterocyclic six-membered rings containing up to 5 heteroatoms, wherein the heteroatoms in the 5- or 6-membered ring can be the same or different and are oxygen, sulphur or nitrogen atoms and, can carry an oxygen atom on one or more nitrogen, atoms, and the five- and six-membered rings can be unsubstituted or substituted at least once by $C_1$–$C_6$-alkyl, $C_1$–$C_6$-alkoxy, $C_1$–$C_6$-alkylthio, hydroxyl, nitro, amino, halogen or cyano; or when X represents a valency bond, besides the above-mentioned groups, $R_1$ can also be hydrogen, hydroxyl, mercapto amino or $C_1$–$C_8$-alkyl, $C_3$–$C_6$ -cycloalkenyl, $C_2$–$C_8$ -alkenyl, $C_3$–$C_6$-cyclo-alkenyl, $C_2$–$C_8$ alkynyl, $C_1$–$C_8$-haloalkyl, $C_1$–$C_8$ hydroxyalkyl, $C_1$–$C_8$ alkoxyalkyl, $C_1$–$C^8$ carboxyalkyl, $C_1$–$C_8$ alkoxycarbonyl $C_1$–$C_8$-alkyl, $C_1$–$C_8$-alkylthio, formylamino-$C_1$–$C_8$-alkyl or pyridylcarbonylamino, X is a valency bond or an $C_1$–$C_8$ alkylene or vinylene, A is nitrogen or—$CR_5$ wherein $R_5$ is hydrogen, cyano, $C_1$–$C_7$-alkyl, $C_2$–$C_7$ alkenyl, $C_3$–$C_7$ cycloalkyl, $C_3$–$C_7$-cycloalkenyl, $C_1$–$C_7$-alkylcarbonyl, $C_1$–$C_7$- alkoxycarbonyl, carboxyl, aminocarbonyl, $C_1$-$C_7$-alkylaminocarbonyl, di-$C_1$-$C_7$-alkylaminocarbonyl or aryl, B is oxygen, sulphur or =$NR_6$ wherein $R_6$ is hydrogen or $C_2$-$C_6$-alkyl, or B is =$CR_7R_8$, wherein $R_7$ is hydrogen, $C_1$-$C_6$-alkyl, $C_2$-$C_6$-alkenyl or $C_3$-$C_7$-cycloalkyl and $R_8$ is hydrogen, cyano, $C_1$-$C_6$-alkyl, $C_2$-$C_6$-alkenyl or a carbonyl substituted by hydroxyl, $C_1$-$C_6$-alkyl $C_1$-$C_6$-alkoxy amino, $C_1$-$C_6$-alkylamino, di-$C_1$-$C_6$-alkylamino or hydrazino, or $R_7$ and $R_8$ together form an $C_1$-$C_6$-alkylidene or $C_3$-$C_7$-cycloalkyliden, or $R_7$ and $R_8$, together with the carbon atom to which they are attached, form a $C_3$-$C_7$-spirocycle; and the tautomers, optically-active forms and racemic mixtures thereof and the physiologically acceptable salts thereof with inorganic and organic acids in a pharmaceutically acceptable carrier.

2. The method of claim 1, comprising treating said conditions with a pharmaceutically effective amount of a compound of Formula I wherein $R_1$ is a phenyl radical of formula (II) wherein $R_2$ is hydrogen, halogen, cyano, nitro, amino or a methanesulphonyloxy, trifluoromethanesulphonyloxy, methanesulphonylamino, trifluoromethanesulphonylamino, methanesulphonylmethylamino, trifluoromethanesulphonylmethylamino, methylsulphinylmethyl, methylsulphonylmethyl, aminocarbonyl, aminosulphonyl, methylaminosulphonyl, dimethylaminosulphonyl, acetylamino, methylthio, methylsulphinyl, methylsulphonyl, hydroxyl, allyloxy, methyl, methoxy, propargyloxy, cyanomethoxy, methoxycarbonylmethoxy, dimethylamino, trifluoromethyl or 1-imidazolyl, $R_3$ is hydrogen, chlorine, hydroxyl, methyl, methoxy or dimethylamino, and $R_4$ is hydrogen or methoxy; or $R_1$ is pyrrolyl, furanyl, thiophenyl, pyrazolyl, imidazolyl, isothiazolyl, thiazolyl, oxazolyl, triazolyl, tetrazolyl, thiadiazolyl, isoxazolyl, oxadiazolyl, pyridinyl, N-oxypyridinyl, pyrazinyl, pyrimidinyl, N,N'-dioxypyrimidinyl, pyridazinyl, oxazinyl, thiazinyl, triazinyl, tetrazinyl or a methyl-, ethyl-, methoxy-, ethoxy-, methylthio-, ethylthio-, or chloro-substituted derivative thereof or, when X is a valency bond, besides the above-mentioned groups $R_1$ is hydrogen, hydroxyl, mercapto, amino, methyl, ethyl, propyl, butyl, pentyl, hexyl, vinyl propenyl, propynyl, cyclopentenyl, cyclohexyl, trifluoromethyl or methylthio, X is a valency bond, ethylene or vinylene, A is nitrogen or—CH, B is oxygen, sulphur or=$NR_6$, wherein $R_6$ is methyl, ethyl or propyl, or B is=$CR_7R_8$, wherein $R_7$ is hydrogen or methyl and $R_8$ is methyl, ethyl or isopropyl, or $R_7$ or $R_8$, together with the carbon atom to which they are attached, form a spirocyclopentyl ring.

3. The method of claim 1 or claim 2 comprising treating said conditions with a pharmaceutically effective amount of a compound of Formula I wherein when $R_1$ is Formula II then $R_2$, $R_3$ and $R_4$ are methanesulphonyloxy, ethanesulphonyloxy, n-propanesulphonyloxy, isopropanesulphonyloxy, trifluoromethanesulphonyloxy, methylsulphenylmethyl, ethylsulphenylmethyl, n-propylsulphenylmethyl, methylsulphinylmethyl, ethylsulphinylmethyl, n-propylsulphinylmethyl, methylsulphonylmethyl, ethylsulphonylmethyl, n-propylsulphonylmethyl, methanesulphonylamino, ethanesulphonylamino, n-propanesulphonylamino, trifluoromethanesulphonylamino, N-methyl-methanesulphonylamino, N-ethylmethanesulphonylamino, N-methyl-ethanesulphonylamino, N-ethylethanesulphonylamino, N-isopropylethanesulphonylamino, N-methyl-n-propanesulphonylamino, N-n-propyl-propanesul-phonylamino, N-methyltrifluoromethanesulphonylamino, N-ethyltrifluoromethanesulphonylamino, N-isopropyl-trifluoromethanesulphonylamino, methoxycarbonyl, ethoxycarbonyl, propoxycarbonyl, isopropoxycarbonyl, methylaminocarbonyl, ethylaminocarbonyl, dimethylaminocarbonyl, di-n-propylaminocarbonyl, N-methyl-ethylaminocarbonyl, trifluoromethyl, methylaminosulphonyl, ethylaminosulphonyl, n-propylaminosulphonyl, n-butyl aminosulphonyl, n-pentylaminosulphonyl, dimethylaminosulphonyl, diethylaminosulphonyl, di-n-propylaminosulphonyl, N-methyl-isopropylaminosulphonyl, acetylamino, propionylamino, methylcarbonylamino, ethylaminocarbonylamino and propylaminocarbonylamino, methyl, ethyl, propyl, methoxy, ethoxy, propoxy, allyloxy, but-2-enyloxy, but-3-enyloxy, pent-2enyloxy, propargyloxy, but-2-ynyloxy, but-3-ynyloxy, cyanomethoxy, cyanoethoxy, methoxycarbonylmethoxy, methoxycarbonylethoxy, methylthio, ethylthio, methylsulphinyl, ethylsulphinyl, methylsulphonyl and ethylsulphonyl;

and wherein the sulphonyl groups substituted by cyclic amino are selected from the group consisting of morpholino, thiomorpholino, pyrrolidino, piperidino and hexamethyleneiminosulphonyl.

4. The method of claim 1 or claim 2 comprising treating said conditions with a compound of formula I wherein $R_1$ is a phenyl of formula II and wherein the monosubstituted phenyl compounds are hydroxy-, $C_1$-$C_3$-alkyl-, $C_1$-$C_3$-alkoxy-, allyloxy-, propargyloxy-, cyanomethoxy-, methoxycarbonylmethoxy-, halo-, nitro-, cyano-, aminocarbonyl-, methoxycarbonyl-, amino-, $C_1$-$C_3$-dialkylamino-, $C_1$-$C_3$-alkylthio-, $C_1$-$C_3$-alkyl-sulphinyl-, $C_1$-$C_3$-alkylsulphonyl-, $C_1$-$C_3$-alkylsulphonyloxy- and 1-imidazolyl-phenyls, wherein the substituent is in the 2-, 3- or 4-position, and disubstituted phenyls are $C_1$-$C_3$ alkanesulphonyloxy, trifluoromethylsulphonyloxy, $C_1$-$C_3$ alkylsulphenylmethyl, $C_1$-$C_3$ alkylsulphinylmethyl, $C_1$-$C_3$ alkylsulphonylmethyl, $C_1$-$C_3$ alkylsulphonylamino, $C_1$-$C_3$ N-alkyl-alkylsulphonylamino, trifluoromethylsulphonylamino, N-alkyl-trifluoromethylsulphonylamino, or carbonyl groups substituted by hydroxy, alkoxy, amino, $C_1$-$C_3$ alkylamino or $C_1$-$C_3$ dialkylamino or sulphonyl substituted by amino, $C_1$-$C_3$ dialkylamino or morpholino, $C_1$-$C_3$ alkylaminosulphonyl, $C_1$-$C_3$ alkylcarbonylamino carbonylamino, aminocarbonylamino or N-alkyl -aminocarbonylamino, halogen, hydroxyl, cyano, nitro or amino $C_1$-$C_3$ alkyl, $C_1$-$C_3$ alkoxy allyloxy, propargyloxy, cyanomethoxy, methoxycarbonylmethoxy, $C_1$—$C_3$ dialkylamino, $C_1$-$C_3$ alkylthio, $C_1$-$C_3$ alkylsulphonyl, $C_1$-$C_3$ alkylsulphonyl or 1-imidazolyl radicals, in which the two substituents can be the same or different and can be in the 2,3-, 2,4- 2,5-, 2,6-, 3,4- and 3,5- positions, and trisubstituted phenyls comprise hydroxyl and methoxy substituents.

5. The method of claim 4 wherein the disubstituted phenyl is in the 2,4-, 2,5- or 3,4-position.

6. The method of claim 1 or claim 2 comprising treating said conditions with a compound of Formula I wherein $R_1$ is pyrrole, furan, thiophene, pyrazole, imidazole, thiazole, isothiazole, oxazole, isoxazole, triazole, tetrazole, thiadiazole, oxadiazole, pyrazine, N,N'-dioxypyrazine, pyrimidine, N,N'-dioxypyrimidine, pyridazine, oxazine, thiazine, triazine, tetrazine, pyridine or N-oxypyridine, and wherein the above ring is unsubstituted or wherein the substituents thereon are methyl, ethyl, methoxy, ethoxy, methylthio and ethylthio.

7. The method of claim 1 or claim 2 comprising treating said conditions with a compound of Formula I wherein X is a valency bond or methylene, ethylene or vinylene, and when X is a valency bond, $R_1$, is methyl, ethyl, propyl, butyl, pentyl, hexyl, vinyl, propenyl or propynyl, or $R_1$ is cyclopropyl, cyclobutyl, cyclopentyl, cyclohexyl, cyclopentenyl or cyclohexenyl, or $R_1$ is ethoxymethyl, methoxyethyl, ethoxyethyl, carboxymethyl, carboxypropyl, carboxybutyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylethyl, hydroxymethyl, hydroxyethyl, hydroxypropyl or hydroxybutyl, and A is nitrogen or -C-$R_5$ wherein $R_5$ is acetyl, propionyl, methoxycarbonyl, ethoxycarbonyl, aminocarbonyl, methylaminocarbonyl or.dimethylaminocarbonyl, and B is=$NR_6$ wherein $R_6$ is methyl, ethyl, propyl, isopropyl, butyl, 2-butyl or 1,1-dimethylethyl, or B is=$CR_7R_8$ wherein $R_7$ is H, methyl, ethyl, isopropyl, 3-pentyl, cyclopentyl or cyclohexyl and $R_8$ is hydrogen, cyano, carboxyl or methyl, ethyl, isopropyl, 3-pentyl, acetyl, propynyl, methoxycarbonyl, ethoxycarbonyl, aminocarbonyl, methylaminocarbonyl, dimethylaminocarbonyl or hydrazinocarbonyl, or $R_7$ and $R_8$ together with the carbon atom to which they are attached form a spirocyclopropyl, spirocyclobutyl, spirocyclopentyl or spirocyclohexyl ring or $R_7$ and $R_8$ together form an isopropylidene or cyclohexylidine ring 8. The method of claim 1 or 2 comprising treating said conditions with a compound of formula I wherein $R_1$ is a phenyl of formula II wherein $R_2$, $R_3$, $R_4$ is hydrogen, hydroxy chlorine $C_1$-$C_5$-alkyl, $C_1$-$C_5$-alkoxy, $C_2$-$C_5$-alkoxyloxy or trifluoromethyl.

9. The method of claim 1 comprising treating said conditions with a compound of formula I wherein A is nitrogen and B is=$CR_7R_8$ wherein $R_7$ or $R_8$ are hydrogen $C_1$-$C_6$-alkyl or together form a $C_3$-$C_7$ spirocycle.

10. A method for the inhibition of erythrocyte aggregation which comprises treating patients having conditions with need of such inhibition with an effective amount of at least one compound selected from the group consisting of 7,7-dimethyl-2-(2-thienyl) -6, 7-dihydro-3H, 5H -pyrrolo -benzimidazol-6-one 7,7-dimethyl-2-(3,4-dichlorophenyl) -6,7-dihydro-3H,5H-pyrrolo benzimidazol-6-one, 7,7-dimethyl-2-(4-trifluoromethylphenyl) -6,7-dihydro-3H,5H-pyrrolo benzimidazol-6-one, 2'-phenyl-spiro -6'-one, and 2'-(4-methoxyphenyl)-spiro -6'-one or a physiologically acceptable salt thereof in a pharmaceutically acceptable carrier.

11. the method of calim 1, 2, 9 or 10 comprising treating said conditions with an amount of from 10 to 2,000 mg per day per body weight of 75 kg.

UNITED STATES PATENT AND TRADEMARK OFFICE
CERTIFICATE OF CORRECTION

PATENT NO. : 4,981,864  
DATED : January 1, 1991  
INVENTOR(S) : von der Saal et al.

Page 1 of 2

It is certified that error appears in the above-identified patent and that said Letters Patent is hereby corrected as shown below:

| | |
|---|---|
| Col. 3, line 10: | change "N-merhyl" to -- N-methyl --. |
| Col. 5, line 53: | change "dimethyylamino" to -- dimethylamino --. |
| Col. 7, No. 9: | change formula "0.3" to read -- 0.3 $H_2O$ --. |
| Col. 11, line 39: | before "3,3-dimethyl-6-(4-methyl-" insert -- 89 --. |
| Col. 12, line 26 Claim 1: | change "alky lsulphenylmethyl" to -- alkylsulphenylmethyl --. |
| Col. 12, line 62 Claim 1: | change "$C_1$-$C^8$" to -- $C_1$-$C_8$ --. |
| Col. 16, line 14 Claim 8: | change "$C_2$-$C_5$-alkoxyloxy" to -- $C_2$-$C_5$-alkenyloxy --. |
| Col. 16, lines 23-24 (bridge) and 26, 28: | after "pyrrolo" insert -- [2,3-f]. |
| Col. 16, line 29 Claim 10: | formula should read as follows: -- 2'-phenyl-spiro [cyclopentane-1,7'-6',7'-dihydro-3'H,5'H-pyrrolo [2',3'f]-benzimidazol]-6'-one --. |

UNITED STATES PATENT AND TRADEMARK OFFICE
CERTIFICATE OF CORRECTION

PATENT NO. : 4,981,864

DATED : January 1, 1991

INVENTOR(S) : von der Saal et al.

It is certified that error appears in the above-identified patent and that said Letters Patent is hereby corrected as shown below:

Col. 16, line 30
    Claim 10:     The formula should read as follows:

-- 2'-(4-methoxyphenyl)-spiro-[cyclopentane-1,7'-6',7'-dihydro-3'H,5'H-pyrrolo-[2',3'f] benzimidazol]-6'-one --.

Signed and Sealed this

Twenty-second Day of December, 1992

*Attest:*

DOUGLAS B. COMER

*Attesting Officer*      *Acting Commissioner of Patents and Trademarks*